United States Patent [19]

Ewalt et al.

[11] Patent Number: 4,610,672
[45] Date of Patent: Sep. 9, 1986

[54] SYRINGE LOCKING DEVICE

[75] Inventors: Paul R. Ewalt, St. Charles; Harold G. Leigh; Richard W. Gilson, both of St. Louis, all of Mo.

[73] Assignee: Sherwood Medical Company, St. Louis, Mo.

[21] Appl. No.: 743,127

[22] Filed: Jun. 10, 1985

[51] Int. Cl.⁴ .......................................... A61M 5/315
[52] U.S. Cl. ................................................. 604/220
[58] Field of Search ............... 604/220, 207, 208, 209, 604/210, 211, 228

[56] References Cited

U.S. PATENT DOCUMENTS

| | | | |
|---|---|---|---|
| 2,869,541 | 1/1959 | Helmer et al. | 604/210 |
| 2,959,170 | 11/1960 | Laub | 604/220 |
| 3,747,812 | 7/1973 | Karman et al. | 604/220 |
| 3,938,505 | 2/1976 | Jamshidi | 128/2 B |
| 4,064,879 | 12/1977 | Leibinsohn | 604/210 |
| 4,386,606 | 4/1983 | Tretinyak et al. | 604/220 |

FOREIGN PATENT DOCUMENTS 2810370 9/1979 Fed. Rep. of Germany ...... 604/208

Primary Examiner—John D. Yasko
Attorney, Agent, or Firm—Stanley N. Garber; Andrew J. Beck; William R. O'Meara

[57] ABSTRACT

A locking device attached to the exterior of a syringe barrel includes a flat body having a circular opening therein for passage of a syringe plunger reciprocatably therethrough. Arms depend from the flat body to frictionally hold the device against rotation with respect to the syringe barrel when a syringe plunger is rotated to engage the locking device. At least two ridges extend chordally across the circular opening, the distance between the ridges being selected so that the ridges engage the syringe plunger when the plunger is oriented in one position but not when the plunger is oriented in another position.

15 Claims, 12 Drawing Figures

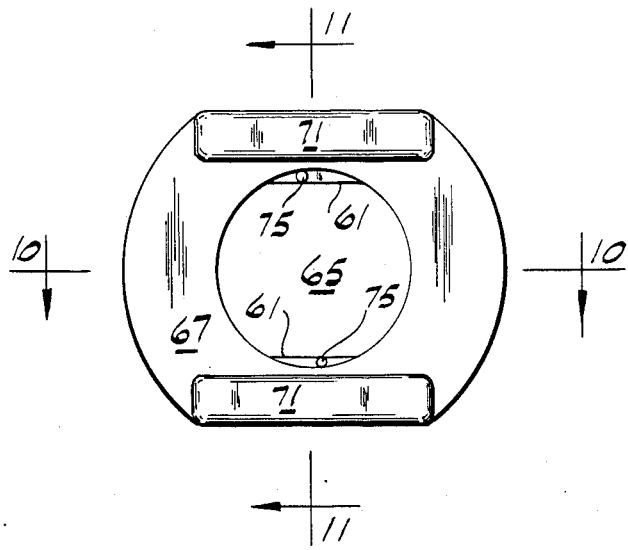
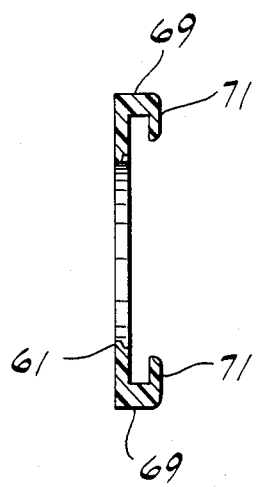
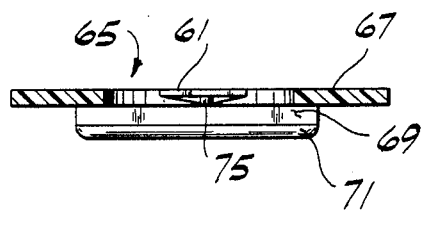
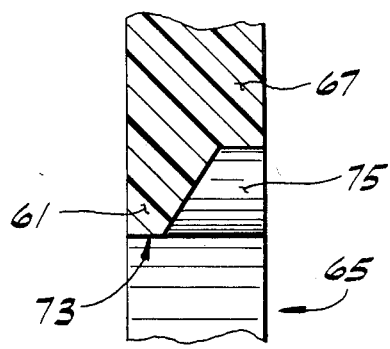

SYRINGE LOCKING DEVICE

BACKGROUND OF THE INVENTION

This invention relates to medical devices and more particularly to locking devices for setting and holding partial vacuums drawn by syringes.

There are several devices known for restraining a syringe plunger in an extended position while a vacuum is held in the syringe barrel in front of the plunger piston. Such devices might include stepped stops on the plunger such as are shown in U.S. Pat. Nos. 3,882,849 and 3,938,505. These stepped stop devices, however, are not capable of a continuous range of partial vacuums but instead provide only discrete vacuum levels corresponding to the steps on the plunger. Devices which can provide continuous ranges of partial vacuums are known, but these typically require a separate moving part such as the cam shown in U.S. Pat. No. 4,386,606. Such moving parts may be relatively difficult to manufacture and to use, and may be less reliable than a device without such an additional moving part. Moreover, all of these prior art devices appear to require that the standard syringe be modified in some way to accept the locking device.

SUMMARY OF THE INVENTION

Among the aspects and features of the present invention is the provision of a locking device for a syringe which is easy to use; the provision of such a device which does not require an additional moving part; the provision of such a device which provides a continuous range of partial vacuums; the provision of such a device which is economical to manufacture; the provision of such a device which may be easily installed on currently available syringes; and the provision of such a device which is reliable in operation. Other features and aspects will be in part apparent and in part pointed out hereinafter.

Briefly, the device of the present invention includes a generally flat body and arms adapted to fit exteriorly of the syringe barrel for holding the device against rotation when in use on a syringe barrel. A generally circular opening in the body allows passage of a syringe plunger reciprocatably therethrough. At least two ridges extend chordally across the generally circular opening, the ridges being spaced from each other a distance less than the diameter of the generally circular opening.

In another aspect, the present invention includes a syringe barrel and a locking device. The locking device has a generally flat body, is mounted on the exterior of the barrel and held against rotation with respect to the barrel. A generally circular opening in the device body provides for passage of a syringe plunger reciprocatably therethrough. At least two ridges extend chordally across the generally circular opening, the ridges being spaced from each other a distance less than the diameter of the generally circular opening.

BRIEF DESCRIPTION OF THE DRAWINGS

FIG. 9 is a rear plan of the locking device of the present invention;

FIG. 10 is a section, taken along line 10—10 of FIG. 1, showing additional detail of the locking device;

FIG. 11 is a section, taken along line 11—11 of FIG. 1, showing additional detail of the locking device; and FIG. 12 is an enlarged view of a portion of FIG. 11.

Similar reference characters indicate similar parts throughout the several views of the drawings.

DESCRIPTION OF THE PREFERRED EMBODIMENT

Figure 1:
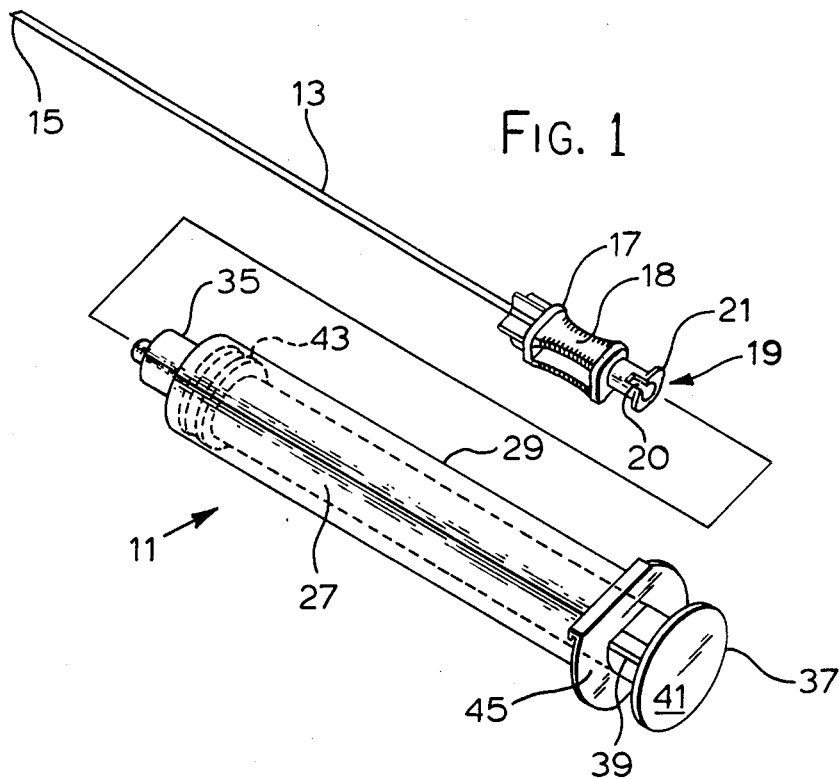
FIG. 1 is a exploded perspective of aspirating biopsy needle apparatus with locking device of the present invention.

Turning now to the drawings, there is shown (FIG. 1) soft tissue aspiration biopsy apparatus 11 which illustrates the use of the locking device of the present invention. Apparatus 11 includes a biopsy needle 13 with a hollow core for receiving a tissue specimen or sample. The needle has a cutting tip 15 at its distal end and is secured to a hub 17 at its opposite, proximal end. Hub 17 has a finger-grip 18 by which it can be grasped for insertion of needle 13 into a body. Hub 17 also has a hollow core, indicated at 19, and a keyway 20 extending distally from its proximal end. Hub 17 terminates at its proximal end in a male luer-lock fitting 21 which is matingly engageable with a corresponding female luer-lock fitting 35 disposed at the distal end of a barrel 27 of a syringe 29. When needle hub 17 is secured by means of the luer-lock fitting to syringe 29, the interior of the needle is in fluid communication with the interior of barrel 27 so that partial vacuums generated inside the barrel are applied to the hollow core of biopsy needle 13.

Syringe 29 further includes a plunger 37 disposed in the syringe barrel, which plunger is reciprocable with respect to the barrel by means of a plunger shaft 39 and a handle 41 attached thereto. Shaft 39 consists of four ribs, each of which extends out from the axis of the shaft at right angles to its neighbors and terminates at its distal end with a plunger tip 43 which slidingly engages the inner wall of barrel 27 to form a seal. A locking device 45 of the present invention is disposed at the proximal end of barrel 27, is exterior thereto, and constitutes means for locking the plunger shaft with respect to the barrel to immobilize the plunger at any desired position with respect to the barrel, whereby any of a desired continuous range of partial vacuums may be applied to the core of biopsy needle 13. Locking device 45 is fixed against rotation with respect to the barrel and may be engaged by the plunger shaft as discussed below to lock shaft 39 against longitudinal movement with respect to barrel 29.

Figure 2:
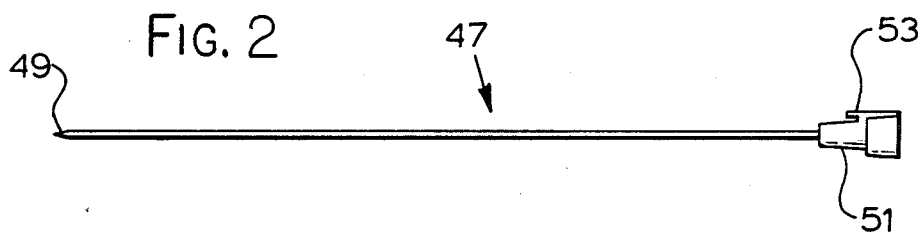
FIG. 2 is a side elevation of a stylet for use with the apparatus of FIG. 1.
Figure 3:
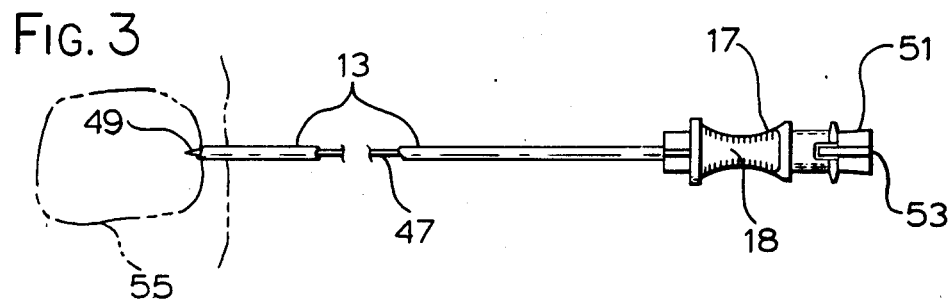
FIG. 3 is a plan of the apparatus of the present invention including the stylet of FIG. 2 penetrated into a body to the site of a tissue from which a specimen is to be taken.

Apparatus 11 also includes a stylet 47 (FIG. 2) having a conical pointed tip 49 at one end and a hub 51 at the other. Hub 51 includes a key 53 sized to fit in keyway 20 of biopsy needle hub 17 to prevent relative rotation of the biopsy needle and the stylet during insertion of the biopsy needle (as shown in FIG. 3) into a body from which a specimen is to be taken. Stylet 47 is sized to extend through the hollow cores of biopsy needle 13 and hub 17 so that the pointed tip of the stylet extends past cutting tip 15 of the needle when the stylet is fully inserted into needle 13. This prevents coring as the needle is advanced into the body and the concomitant contamination of the specimen with extraneous tissue. The outside diameter of stylet 47 is, for example and not by way of limitation, approximately 5/10,000 of an inch (0.01 mm) smaller than the inside diameter of needle 13 to permit the stylet to be easily inserted into needle 13 and removed therefrom while still preventing coring. Stylet 47 is completely removable from needle 13 so that once the needle and stylet have been inserted to a desired location in the body as shown in FIG. 3 adjacent the tissue 55 to be sampled, the stylet may be removed from the biopsy needle. Syringe 29 with needle hub 23 attached thereto may be prefilled with a small amount of saline solution at this or any suitable earlier time and then attached to the hub of biopsy needle 13. Once hub 17 is secured to the syringe, the interior of needle 13 is in fluid communication with the interior of barrel 27.

Figure 4:
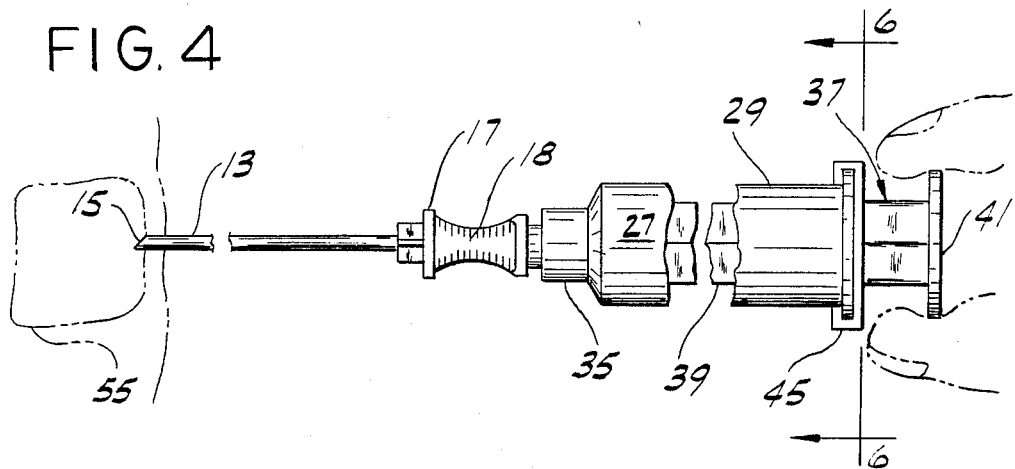
FIG. 4 is a plan of the assembled apparatus of FIG. 1 immediately prior to the taking of a specimen.
Figure 5:
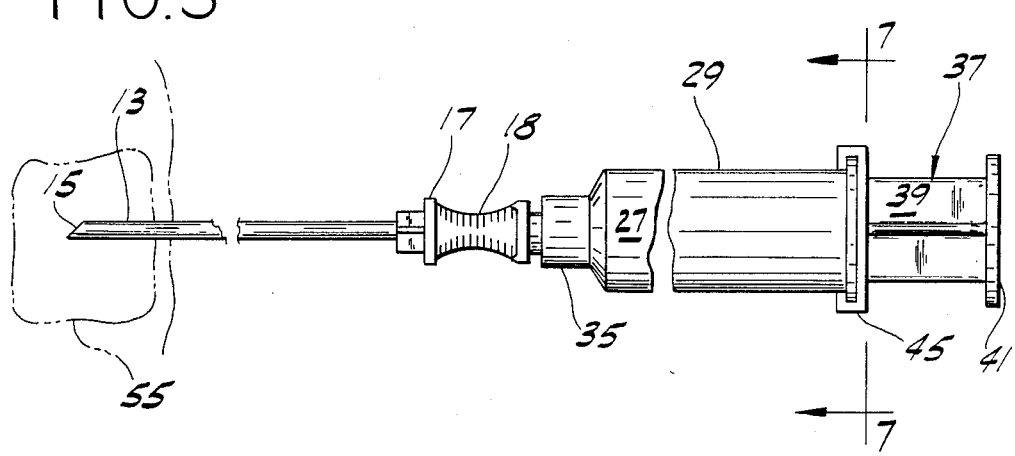
FIG. 5 is a plan of the assembled apparatus of FIG. 1 immediately after the taking of a specimen.

To draw a partial vacuum in needle 13, the user thereupon withdraws the plunger 37 with respect to the barrel 27 from the position shown in FIG. 4 to any desired position such as that shown in FIG. 5. When the desired vacuum is attained, the user rotates the plunger shaft approximately 45° with respect to the barrel to lock it in place (as is explained below) and pushes the assembly into the tissue to be sampled as shown in FIG. 5. As needle 13 is forced into the tissue, tip 15 cuts off a specimen and the vacuum in needle 13 draws it into the needle. Upon removal of the needle from the body, the specimen can be expelled into a suitable receptacle by rotating the plunger shaft to unlock the plunger with respect to the barrel and then pushing the plunger toward the distal end of the syringe to expel the specimen.

Locking device 45 is a single molded piece of phenylene oxide or some other suitable hard resin such as polypropylene having a hardness on the Rockwell scale of, for example, R95-100. Syringe barrel 27 includes a finger grip 59 over which locking device 45 is slid during the manufacturing process. More specifically, finger grip 59 has two flat edges and two rounded edges. Device 45 has generally the same outline, but is larger, and has a pair of ears 69 (see FIGS. 10 and 11) which extend over and behind the flat edges of the finger grip to hold the device against rotation with respect to the barrel once it is placed over the finger grip. Device 45 is dimensioned to provide a friction fit between itself and the finger grip although the tightness of the fit is not critical to the present invention.

Figure 6:
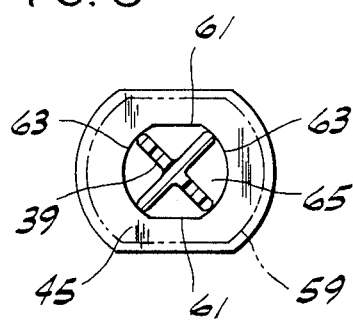
FIG. 6 is a section, taken along line 6—6 of FIG. 4, showing a locking device of the present invention with part of the syringe shown in phantom.
Figures 7, 8:
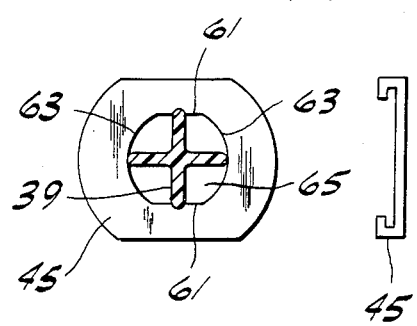
FIG. 7 is a section, taken along line 7—7 of FIG. 5, showing the plunger of the syringe locked against movement with respect to the barrel by the locking device of FIG. 6.
FIG. 8 is a side elevation of the locking device of the present invention.

Device 45 has a pair of generally flat camming surfaces 61 (FIG. 6), which in the embodiment shown are parallel to the flat edges of device 45 but which may assume other orientations, and a pair of curved surfaces 63 therebetween which define a generally circular opening 65 through which the shaft of plunger 37 reciprocatably passes. When the plunger shaft has the orientation shown in FIG. 6, the plunger shaft is easily movable with respect to locking device 45 along its longitudinal axis. However, when shaft 39 is rotated to the position shown in FIG. 7 it is held against further longitudinal movement because the distance between flat surfaces 61 is less than the transverse width of the plunger shaft measured along the ribs. It is desirable to choose a material such as polypropylene for the plunger shaft that will deform or cut slightly when forced into contact with flat surfaces 61. Alternatively, the material of locking device 45 may be selected to deform. In the preferred embodiment, a harder material such as the glass-filled polyester sold by Du Pont under the trade name Rynite and having a hardness of R120 on the Rockwell scale is used for the locking device. In either case, the resulting tight friction fit prevents relative motion between the barrel and the plunger once the plunger is locked in place, thus freeing the user's hands.

Device 45 (shown in more detail in FIGS. 9 to 12) has a generally flat body 67 in which opening 65 is centered for passage of syringe plunger 39 reciprocatably therethrough. Generally flat camming surfaces 61 are seen from FIGS. 9 and 10 to be ridges which extend chordally across opening 65 and which are substantially parallel to each other. A pair of ears 69 extend out perpendicularly from the plane of flat body 67 toward the distal end of the syringe, each ear 69 terminating in a inwardly extending lip 71. Ears 69 and lips 71 are dimensioned to slide over finger grip 59 of the syringe and thus constitute means adapted to fit exteriorly of the syringe barrel for holding the locking device against rotation while in use on barrel 27.

Ridges 61 are not as thick as flat body 67 (see FIGS. 10 and 12) and are tapered away from the central opening for strength, ease of manufacture, and to provide a relatively thin cutting surface 73 for cutting into or suitably depressing the rib of plunger shaft 39 which is brought into rotation therewith. To ensure that the plunger shaft upon rotation to the locking position shown in FIG. 8 does not rotate past the locking position, and hence free the plunger inadvertently, a post or stop 75 is provided on each ridge 61. Posts 75 are disposed on opposite sides of a center line of opening 65 which extends perpendicular to both ridges to allow the plunger shaft to be rotated to the position shown in FIG. 8 and are thicker than the ridges (that is they extend distally out from the ridges). As shown in FIG. 13, post 75 is the same thickness as flat body 67 and thus provides a positive stop for plunger shaft 39.

In view of the above, it can be seen that the aspects of the invention are achieved and other advantageous results attained.

While a preferred embodiment of the present invention has been described, it should be understood that various changes, adaptations, and modifications may be made therein without departing from the spirit of the invention and the scope of the appended claims.

What is claimed is:

1. A locking device for attachment to the exterior of a syringe barrel, comprising:

a generally flat body;

means adapted to fit exteriorly of the syringe barrel for holding the device against rotation when in use on a syringe barrel;

a generally circular opening in the body for passage of a syringe plunger reciprocatably therethrough; and at least two ridges extending chordally across the generally circular opening, said ridges being spaced from each other a distance less than the diameter of the generally circular opening and said ridges having a thickness that is less than the thickness of the body.

2. A locking device as set forth in claim 1 wherein the ridges are sloped so that the thickness of each ridge decreases toward the generally circular opening.

3. A locking device as set forth in claim 1 further including a stop on each ridge of greater thickness than the remainder of the ridge.

4. A locking device as set forth in claim 3 wherein the ridges are generally parallel to each other and the stops are on opposite sides of a center line of the generally circular opening drawn perpendicular to the ridges.

5. A locking device for attachment to the exterior of a syringe barrel, comprising:
   a generally flat body;
   means adapted to fit exteriorly of the syringe barrel for holding the deivce against rotation when in use on a syringe barrel;
   a generally circular opening in the body for passage of a syringe plunger reciprocatably therethrough; and
   at least two ridges extending chordally across the generally circular opening, said ridges being spaced from each other a distance less than the diameter of the generally circular opening, and said ridges being sloped so that the thickness of each ridge decreases toward the generally circular opening.

6. A locking device for attachment to the exterior of a syringe barrel, comprising:
   a generally flat body;
   means adapted to fit exteriorly of the syringe barrel for holding the device against rotation when in use on a syringe barrel;
   a generally circular opening in the body for passage of a syringe plunger reciprocatably therethrough;
   at least two ridges extending chordally across the generally circular opening, said ridges being spaced from each other a distance less than the diameter of the generally circular opening; and
   a stop on each ridge of greater thickness than the remainder of the ridge.

7. A locking device as set forth in claim 6 wherein the ridges are generally parallel to each other and the stops are on opposite sides of a center line of the generally circular opening drawn perpendicular to the ridges.

8. A syringe comprising a barrel having distal and proximal ends, a plunger reciprocatably disposed in the barrel, and a locking device, said locking device having a generally flat body and being mounted on the proximal end of the barrel exterior thereto, and held against rotation with respect to the barrel, said locking device further having a generally circular opening in the body for passage of the plunger reciprocatably therethrough, and further having at least two ridges extending chordally across the generally circular opening, said ridges being sloped so that the thickness of each ridge decreases toward the generally circular opening.

9. A syringe comprising a barrel having distal and proximal ends, a plunger reciprocatably disposed in the barrel, and a locking device, said locking device having a generally flat body and being mounted on the proximal end of the barrel exterior thereto, and held against rotation with respect to the barrel, said locking device further having a generally circular opening in the body for passage of the plunger reciprocatably therethrough, and further having at least two ridges extending chordally across the generally circular opening and a stop on each ridge of greater thickness than the remainder of the ridge which is engageable by the plunger upon rotation thereof about the longitudinal axis of the plunger.

10. The syringe as set forth in claim 9 wherein the ridges of the locking device are generally parallel to each other and the stops are on opposite sides of a center line of the generally circular opening drawn perpendicular to the ridges.

11. A syringe comprising a syringe barrel having a bore therein and distal and proximal ends, a syringe plunger locking device fixed to said proximal end of said barrel, said locking device including locking means projecting into said bore and constructed of a first material, and a syringe plunger axially and rotatably movable within said bore, said plunger having a longitudinal axis and radial projecting means fixedly projecting radially of said longitudinal axis, said projecting means constructed of a second material, said plunger being rotatable from a first position wherein said plunger is axially movable in said bore to a second position wherein said projecting means contact said locking means, one of said materials being softer than the other of said materials whereby upon rotation of said projection means into contact with said locking means said one of said materials is deformed by the other of said materials to thereby axially lock said plunger to said locking device and in said barrel.

12. The syringe of claim 11 wherein said projecting means are constructed of said one material softer than said other material and is scored thereby.

13. The syringe of claim 11 wherein said projecting means are provided along substantially the full axial length of the portion of said plunger adapted to be axially moved into and out of said bore whereby said plunger is adapted to be locked at any point along the length of said portion.

14. The syringe of claim 12 wherein both of said materials are plastic, said other material having a Rockwell hardness of about R120.

15. The syringe of claim 11 wherein said locking device has a generally flat body and a generally circular opening therein for passage of said plunger for reciprocating therethrough, said locking means including at least two ridges extending chordally across said generally circular opening.

* * * * *